US012576372B2

(12) United States Patent　(10) Patent No.: US 12,576,372 B2

Ridgway　(45) Date of Patent: Mar. 17, 2026

(54) METHOD AND APPARATUS TO MIX GAS WITH A FLUID

(71) Applicant: Soave Enterprises LLC, Detroit, MI (US)

(72) Inventor: James W. Ridgway, Manistique, MI (US)

(73) Assignee: Soave Enterprises LLC, Detroit, MI (US)

( * ) Notice: Subject to any disclaimer, the term of this patent is extended or adjusted under 35 U.S.C. 154(b) by 853 days.

(21) Appl. No.: 17/855,190

(22) Filed: Jun. 30, 2022

(65) Prior Publication Data

US 2024/0001316 A1　Jan. 4, 2024

(51) Int. Cl.
| | |
|---|---|
| *B01F 25/312* | (2022.01) |
| *A61L 2/14* | (2006.01) |
| *A61L 2/26* | (2006.01) |
| *B01F 23/2326* | (2022.01) |
| *B01F 35/221* | (2022.01) |
| *B01F 101/00* | (2022.01) |
| *C02F 1/30* | (2023.01) |

(52) U.S. Cl.
CPC .......... *B01F 25/31242* (2022.01); *A61L 2/14* (2013.01); *A61L 2/26* (2013.01); *B01F 23/2326* (2022.01); *B01F 25/31232* (2022.01); *B01F 35/2211* (2022.01); *C02F 1/30* (2013.01); *B01F 2101/305* (2022.01); *C02F 2303/04* (2013.01)

(58) Field of Classification Search
CPC ...... A61L 2/14; A61L 2/18; A61L 2/26; B01F 23/2319; B01F 35/2211; C02F 1/30
See application file for complete search history.

(56) References Cited

U.S. PATENT DOCUMENTS

| | | | |
|---|---|---|---|
| 3,074,870 A | 1/1963 | Carswell et al. | |
| 3,852,076 A | 12/1974 | Grasko | |
| 5,863,128 A | 1/1999 | Mazzei | |
| 6,623,635 B2 * | 9/2003 | Barnes ..................... | C02F 1/78 |
| | | | 261/DIG. 42 |
| 9,308,505 B2 | 4/2016 | Spears et al. | |
| 9,352,984 B2 | 5/2016 | Campbell et al. | |
| 10,032,593 B1 * | 7/2018 | Lee ......................... | H01T 23/00 |
| 10,792,625 B2 | 10/2020 | Talamantez et al. | |
| 10,797,472 B1 | 10/2020 | Lee et al. | |

(Continued)

FOREIGN PATENT DOCUMENTS

| | | |
|---|---|---|
| DE | 19951117 A1 | 4/2001 |
| GB | 2514202 A | 11/2014 |

(Continued)

OTHER PUBLICATIONS

Groon, "Variations of O3 productivity according to air flowrates and applied boards of non-thermal plasma", Jeonbuk National University presentation, 12 pages.

(Continued)

*Primary Examiner* — Bobby Ramdhanie

(74) *Attorney, Agent, or Firm* — Harness, Dickey & Pierce, P.L.C.

(57) ABSTRACT

A plasma-activated gas generated by a plasma-activated gas generator is mixed with a liquid in a variety of ways to generate a gas activated liquid. The gas activated liquid may be applied to various items, surfaces, and/or added to fluid volumes to affect chemical specifies and organism therein.

19 Claims, 5 Drawing Sheets

(56) References Cited

U.S. PATENT DOCUMENTS

| | | | |
|---|---|---|---|
| 11,130,104 | B1* | 9/2021 | Lynn ........................ C02F 1/008 |
| 2004/0197244 | A1* | 10/2004 | Kirby ....................... C01B 13/11 |
| | | | 422/186.07 |
| 2010/0038248 | A1 | 2/2010 | Krasik |
| 2010/0126940 | A1 | 5/2010 | Ryu et al. |
| 2014/0069853 | A1 | 3/2014 | Lee et al. |
| 2015/0110932 | A1 | 4/2015 | Thagard et al. |
| 2016/0102025 | A1 | 4/2016 | Nunnally et al. |
| 2016/0228844 | A1 | 8/2016 | Mededovic et al. |
| 2017/0259219 | A1* | 9/2017 | Russell .................... C02F 1/685 |
| 2017/0348447 | A1* | 12/2017 | Lu ............................. A61L 2/14 |
| 2017/0354024 | A1* | 12/2017 | Lu ............................. C02F 1/72 |
| 2018/0057372 | A1 | 3/2018 | Lee |
| 2018/0354823 | A1 | 12/2018 | Lee et al. |
| 2024/0002264 | A1 | 1/2024 | Lee et al. |

FOREIGN PATENT DOCUMENTS

| | | |
|---|---|---|
| KR | 20120111544 A | 10/2012 |
| WO | 2016096751 A1 | 6/2016 |
| WO | 2024006124 A1 | 1/2024 |

OTHER PUBLICATIONS

International Preliminary Report on Patentability and Written Opinion for related International application No. PCT/US2023/025839; date of mailing: Jan. 9, 2025; 8 pages.

"A critical review of the recent developments in micro-nano bubbles applications for domestic and industrial wastewater treatment", Sakr, Mohamed, Maraqa, Hamouda, Hassan, Ali, Jung, Alexandria Engineering Journal, 61:8, pp. 6591-6612 (Feb. 2, 2022) at www.sciencedirect.com/science/article/pii/S1110016821007742?via%3Dihub.

Gururani, P., Bhatnagar, P., Bisht, B. et al. Cold plasma technology: advanced and sustainable approach for wastewater treatment. Environmental Science and Pollution Research, 28, 65062-65082 (2021). https://doi.org/10.1007/s11356-021-16741-x.

Cubas, A. L. V., Machado, M. de M., Machado, M. de M., Moecke, E. H. S., Dutra, A. R. de A., Fiedler, H., & Bueno, P.. (2016). Application of Thermal Plasma for Inertization of Sludge Produced During Treatment of Landfill Leachate. Química Nova, 39(8), 906-913. https://doi.org/10.21577/0100-4042.20160135.

Krishnan, S., et al. "Comparison of various advanced oxidation processes used in remediation of industrial wastewater laden with recalcitrant pollutants." IOP Conference Series: Materials Science and Engineering. vol. 206. No. 1. IOP Publishing, 2017.

EPA, US. "Multi-Industry Per-and Polyfluoroalkyl Substances (PFAS) Study—2021 Preliminary Report." (2021).

United States. Environmental Protection Agency. EPA's Per-and Polyfluoroalkyl Substances (PFAS) Action Plan. 2019.

Talebizadeh, Pouyan, et al. "Evaluation of residence time on nitrogen oxides removal in non-thermal plasma reactor." PloS one 10.10 (2015): e0140897.

Cornerstone, a Tetra Tech Company, "Is non-thermal plasma treatment a viable solution for removing recalcitrant organic compounds from treated landfill leachate?" (Jul. 22, 2015) www.cornerstoneeg.com/2015/07/22/non-thermal-plasma-treatment-viable-solution-removing-recalcitrant-organic-compounds-treated-landfill-leachate/ (pp. 1-3).

Mashal, Ahmad, et al. "Landfill leachate treatment using plasma-Fenton's process." Sixth Jordan International Chemical Engineering Conferenc? (2012): 256-259.

Kasih, Tota Pirdo, et al. "Development of non-thermal plasma jet and its potential application for color degradation of organic pollutant in wastewater treatment." IOP Conference Series: Earth and Environmental Science. vol. 109. No. 1. IOP Publishing, 2017.

B. Jiang, J. Zheng, M. Wu,—Chapter 13—Nonthermal Plasma for Effluent and Waste Treatment, Editor(s): N.N. Misra, Oliver Schlüter, P.J. Cullen, Cold Plasma in Food and Agriculture, Academic Press, 2016, pp. 309-342, ISBN 9780128013656, https://doi.org/10.1016/B978-0-12-801365-6.00013-5. (https://www.sciencedirect.com/science/article/pii/B9780128013656000135).

Misra, N. N., et al. "Nonthermal plasma inactivation of food-borne pathogens." Food Engineering Reviews 3 (2011): 159-170.

Jansen, Kerri. ""Forever chemicals" no more? These technologies aim to destroy PFAS in water." Chem. Eng. News 97 (2019): 28.

PFAS—Clarkson University, Collaboration Key to Environmental Cleanup (Oct. 14, 2019) https://www.clarkson.edu/make-impact/collaboration-key-environmental-cleanup (pp. 1-3).

Crimi, Michelle, et al. "Combined In Situ / Ex Situ Treatment Train for Remediation of Per- and Polyfluoroalkyl Substance (PFAS) Contaminated Groundwater" Clarkson University, ER18-1306 Project Overview, Strategic Environmental Research and Development Program (SERDP), Environmental Security Technology Certification Program (ESTCP).

Thomas Holsen and Selma Mededovic Thagard, "U.S. Air Force Funds Innovative Technology to Improve Groundwater Clean Up", PFAS Clarkston University, Oct. 11, 2017, pp. 1-3, https://www.clarkson.edu/news/us-air-force-funds-innovative-technology-improve-groundwater-clean., Potsdam New York.

Prof. Selma Mededovic Thagard, "Plasma Treatment of Perfluoroalkyl Substances in Ion Exchange Brine Solutions: Reactor Design Challenges and Physicochemical Processes at the Plasma-liquid Interface", Apr. 4, 2018, Michigan Institue for Plasma Science and Engineering, Clarkston University.

Christopher Sales, "Application of Non-Thermal Plasma Technology for the Removal of Per- and Polyfluorinated Substances from Investigation-Derived Wastes", SERDP and ESTCP, Jul. 3, 2018, pp. 1-2, Drexel University ER18-1570, Alexandria, VA.

SERDP and ESTCP Environmental Restoration Program Manager, "Novel Treatment Approaches for PFAS Investigation-Derived Waste in the Subsurface", https://www.serdp-estcp.org/News-and-Events/Blog/Novel-Treatment-Approaches-for-PFAS-Investigation-Derived-Waste-in-the-SubsurfaceJul. 3, 2018, pp. 1-2, SERDP and ESTCP, Alexandria, VA.

Bhawana Adhikari et. al., "Plant Disease Control by Non-Thermal Atmospheric-Pressure Plasma", Frontiers in Plant Science, Feb. 14, 2020, pp. 1-15, vol. 11, Article 77.

Taeho Kwon et. al., "Potential Applications of Non-thermal Plasma in Animal Husbandry to Improve Infrastructure,", In Vivo Journals, Jul. 2019, pp. 1-16, vol. 33, No. 999-1010, Korea Research Institute of Bioscience and Biotechnology, Republic of Korea.

Plasma Science, "The iHPTM Process (ionized Hydrogen Peroxide)", Tomi Environmental Solutions Stermist, pp. 1-4, https://tomimist.com, Beverly Hills, CA.

Fumiyoshi Tochikubo, "Study of Wastewater Treatment by OH Radicals Using DC and Pulsed Corona Discharge over Water", The Japan Society of Applied Science, Apr. 7, 2006, pp. 2743-2748, vol. 45, No. 4A, Tokyo Japan.

Daniel Almarcha et al., "Treatment Efficiency by means of a Nonthermal Plasma Combined with Heterogeneous Catalysis of Odoriferous Volatile Organic Compounds Emissions from the Thermal Drying of Landfill Leachates", Hindawi Publishing Corporation Journal, Dec. 28, 2014, pp. 1-10, vol. 2014, Article ID 831584, Barcelona Spain.

Ravi Srivastava et al., "Using Non-Thermal Plasma to Control Air Pollutants", United State Environmental Protection Agency, Feb. 2005, pp. 1-13, Clean Air Technology Center, North Carolina.

Hee-Jun Kim 1 et. al., "Cold Plasma Treatment for Efficient Control over Algal Bloom Products in Surface Water," MDPI, Jul. 21, 2019, pp. 1-9, Water 2019, 11, 1513, Korea.

International Search Report and Written Opinion of the ISA issued in PCT/US2023/025839, mailed Oct. 16, 2023; ISA/US.

International Search Report and Written Opinion of the ISA issued in PCT/US2024/061423, mailed Apr. 17, 2025; ISA/EP.

* cited by examiner

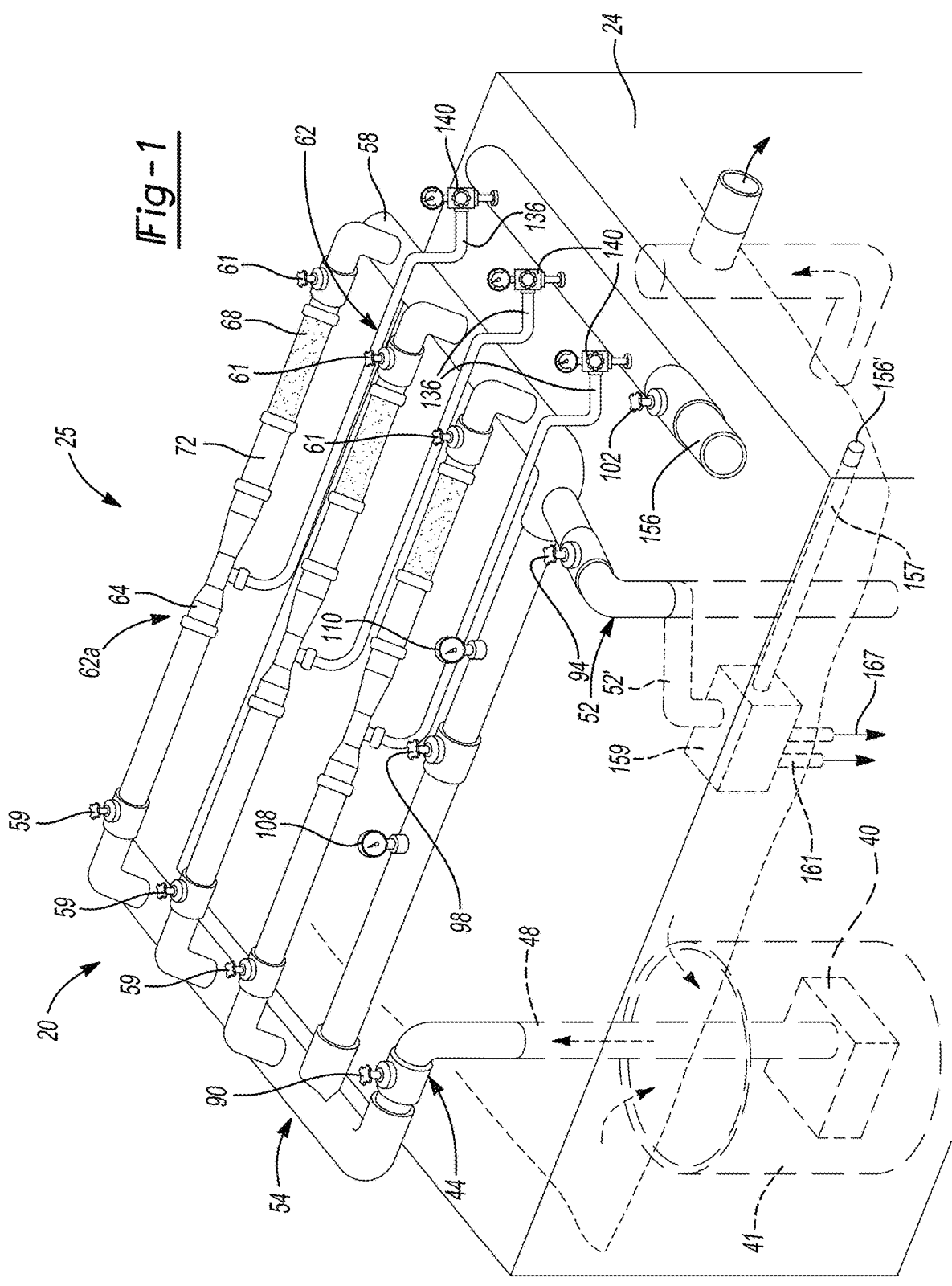
_Fig-1_

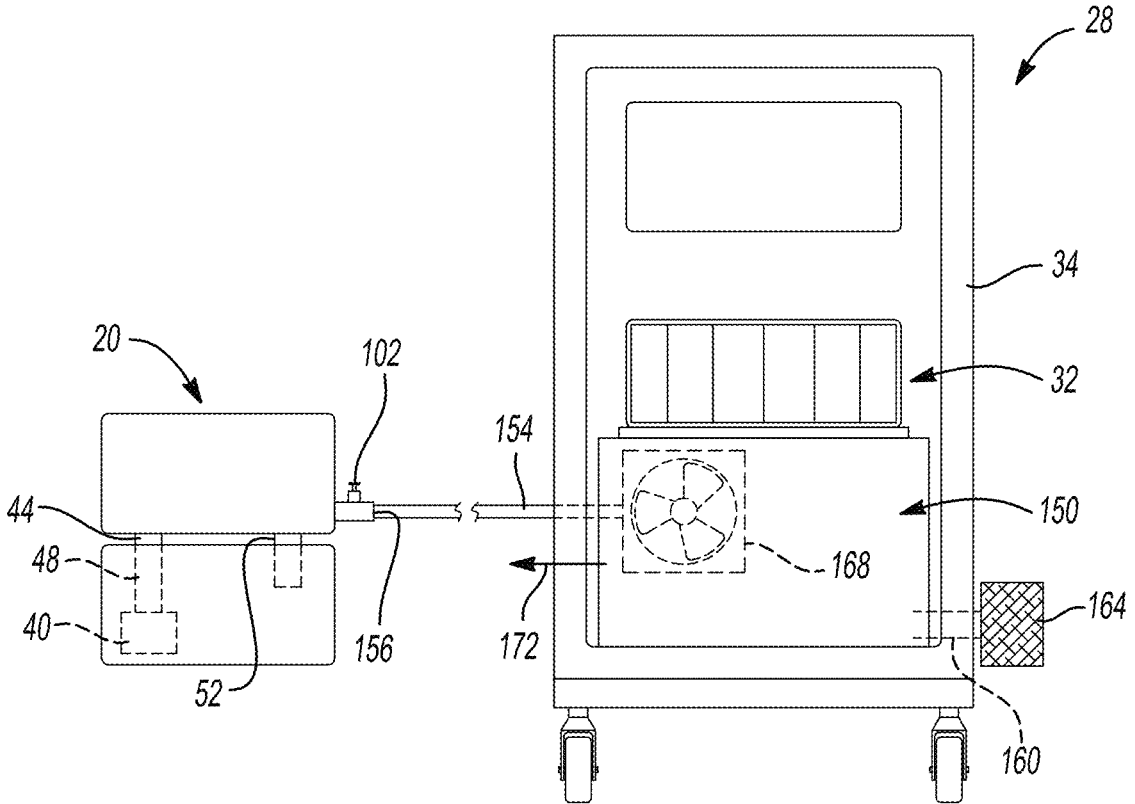
_Fig-5_

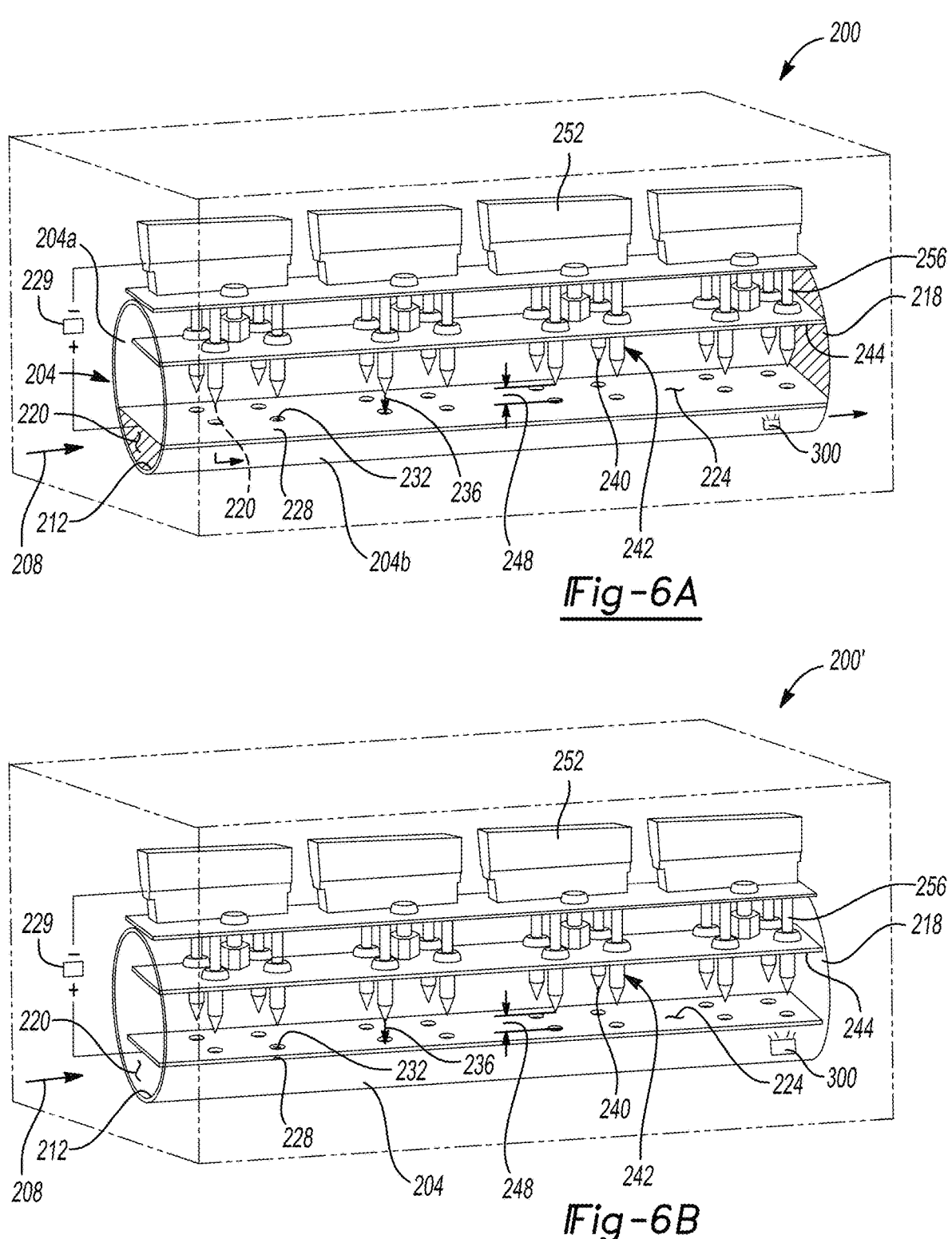
_Fig-6A_
_Fig-6B_

METHOD AND APPARATUS TO MIX GAS WITH A FLUID

FIELD

The subject disclosure relates to a system for infusing gas into a fluid, including infusing a selected generated gas into a selected water volume for destruction and/or neutralization of selected compounds and/or organisms, including chemical and/or biological species within the selected liquid volume.

BACKGROUND

This section provides background information related to the present disclosure which is not necessarily prior art.

A water volume may be treated for various purposes. The purposes may include destruction of selected chemical or biological species. The purposes may include cleaning or sterilization of the water source. The treated water may be then used for general clean water purposes, such as drinking, irrigation, discharge, etc.

In various embodiments, the treated water may be treated with a gas that has passed through a selected mechanism. For example, a corona may be generated through which a gas is passed. For example, a plasma generation system may include that disclosed in U.S. Pat. No. 10,032,593. The plasma generation unit may be used to generate a plasma and a selected gas may pass through a corona in the plasma generation area, such as atmospheric air, and be used to affect organic chemicals and/or organisms.

SUMMARY

This section provides a general summary of the disclosure and is not a comprehensive disclosure of its full scope or all of its features.

A selected gas may be activated in a selected manner. For example, atmospheric air may pass a plasma generation area to generate plasma-activated gas (PAG). The PAG may be a partially or wholly ionized gas composed essentially of photons, ions, and free electrons as well as atoms in their fundamental or excited states possessing a net neutral charge. The PAG may include gas that is generated with a generation system such as that disclosed in U.S. Pat. No. 10,032,593, incorporated herein by reference.

The PAG, particularly when atmospheric air is used as the source gas, may include various chemical species including hydroxyl ions, oxygen radicals, nitrogen radicals, hydrogen peroxide, nitrous oxide, or other selected chemical species. Also, the PAG may rapidly changes as it exits the generation system but forms relatively stable but reactive gases like ozone, hydrogen peroxide, singlet oxygen, nitrous oxide, and other reactive gases.

The concentration of the reactive gases may be dependent on the size and number of the coronas within the plasma generator, the dwell time in the plasma generator, the flow rate of the carrier gas, the distance and time between generation and infusion into carrier fluid (water or gas). The amount of plasma-activated gas needed for a specific application is dependent on the concentration of PAG at the application point, the strength and/or concentration of the species of interest (also referred to as target pollutant), species (such as chemical or biological species), and the difficulty of treatment of the target pollutant. In certain applications, a single pass is sufficient to infuse sufficient reactive gas to destroy the species of interest, for example, blue green algae (Cyanobacteria) are no longer viable after contacting sufficient concentration of PAG. In other applications, the species of interest, like PFAS, are disassociated and reform to other species of PFAS and therefore may require more than one contact with PAG. With PFAS, the chemical structure may be or is disrupted in a single pass, but the PFAS can recombine to become shorter chained PFAS. If these applications, multiple passes may be required to render the chemical non-toxic and become non-associated carbon and fluorine molecules. In certain embodiments, a higher concentration may also be adequate rather than multiple passes to achieve a selected result.

The plasma-activated gas may be moved from a generation volume (e.g., in a PAG generator) to a secondary volume. For example, a fluid mixing system to efficiently mix the PAG with a non-reactive carrier gas and/or mix (e.g., dissolve) the gas into a liquid. The transfer rate of PAG into the liquid is a function to liquid-to-gas surface area, contact time, pressure at the transfer point, and saturation concentration of the individual gas components. Gas Infusion System may involve an aeration system, an infusion system/injection system, and/or a pressurized emulsion system. These systems are designed to increase the concentration of gas while minimizing the loss of gas through excessive bubbles. These systems may be connected to the PAG generator. The PAG generator may be any appropriate generator of PAG. The fluid mixing system may flow or move the PAG to a secondary volume. In various embodiments the PAG can be infused into a target liquid using aeration, spraying the target liquid through a PAG gas chamber, and/or infusion. In various embodiments, for example, one or more venturi flow tubes may be used to infuse the PAG into a selected volume of water. In various embodiments. a venturi member (e.g., a venturi valve) may be used to infuse a selected volume of water with the PAG. The mixing system may attempt to saturate, super-saturate, or achieve a selected concentration of the PAG in the selected liquid. The system can increase gas delivery, optimize gas concentration, and minimize gas loss. One skilled in the art, however, will understand that the fluid mixing system, as discussed herein, may be applied to a selected PAG generation system and may be used for various purposes.

Once the PAG is mixed with a liquid (e.g., water), the mixed PAG and liquid (e.g., PAG infused liquid) may be referred to as gas activated liquid (GAL). The GAL may be used for various purposes. The GAL may be used to clean various items, such as surfaces or surface areas. In addition, the GAL may be used to destroy species of interest, such as problematic chemical or biological species and/or further sterilize or clean larger volumes, such as a water supply, a pond, water body or wastewater basins. The GAL may be used to destroy and/or neutralize various chemical species, biological agents, or the like. Further, the GAL may be used to assist in agriculture and/or aquaculture such as to ensure a clean and healthy environment, to enhance seed germination and growth, and/or control bacteria, virus, and fungus in irrigation systems. The GAL can be used for lake/river/harbor restoration targeting destruction and/or control of blue green algae (cyanobacteria) and/or red tide (Karenia).

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations and are not intended to limit the scope of the present disclosure.

FIG. 1 is a schematic view of a gas infusion system, according to various embodiments;

FIG. 5 is a schematic view of a gas infusion system and activated gas generation system, according to various embodiments;

FIG. 6A is a schematic view of an activated gas generation system, according to various embodiments; and FIG. 6B is a schematic view of an activated gas generation system, according to various embodiments.

Corresponding reference numerals indicate corresponding parts throughout the several views of the drawings.

DETAILED DESCRIPTION

Figure 2:
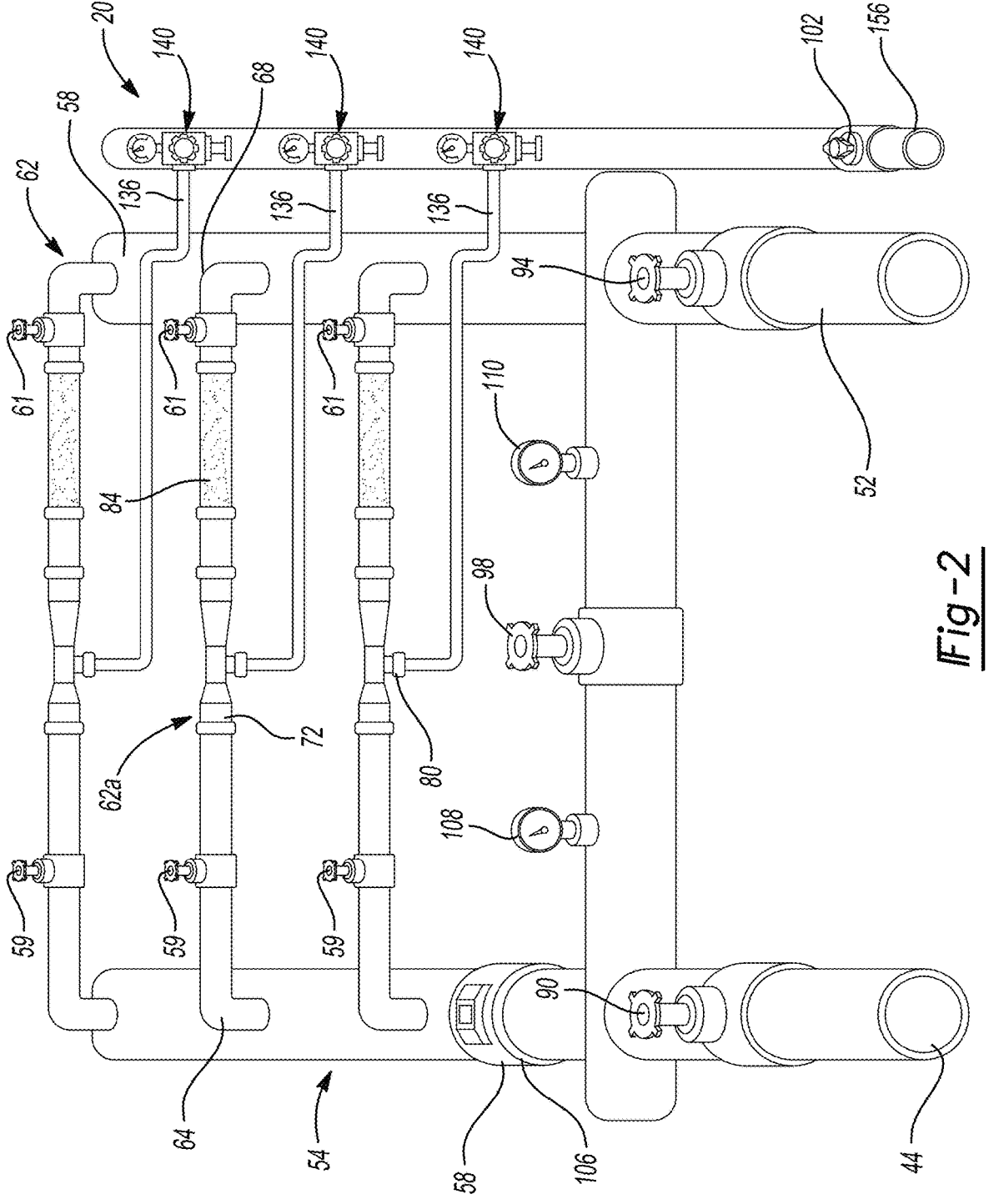
FIG. 2 is a detail schematic view of a portion of the gas infusion system of FIG. 1, according to various embodiments.

Example embodiments will now be described more fully with reference to the accompanying drawings.

With initial reference to FIG. 1, a gas and fluid mixing system is exemplary illustrated as an infusion system 20. As discussed herein, the mixing system may be the infusion system 20, but it is understood by one skilled in the art that the infusion system may be replaced and/or augmented for dissolving the PAG into the liquid. The infusion system 20 may be used to infuse gas into a selected volume of liquid, such as a volume of liquid included within a tank 24. The tank 24 may hold a selected volume of water, such as an auxiliary or treated volume of water. Once the water in the tank has sufficient dissolved PAG, which may be referred to as gas activated liquid (GAL), the GAL from the tank 24 may then be transferred to a secondary or main volume of liquid, such as water, in either a continuous or batch process. Further, it is understood, that the infusion system 20 may be directly connected to the main volume of water and the recirculating treatment in the intermediate or auxiliary volume, for example as contained in the tank 24, may not be necessary. In various embodiments, however, it may be efficient or compact to treat the auxiliary volume of water, such as in the tank 24, to control and optimize the amount of PAG infused and transport or move the auxiliary treated volume of water to a secondary or main volume of water.

Exemplarily discussed herein is water as a liquid that may be infused with the gas and/or may be treated with gas (e.g., plasma activated gas (PAG)) and/or GAL. It is understood, however, that any appropriate liquid may be treated and/or mixed with the PAG unless specifically noted herein. Further, while the following discussion relates and includes a discussion of infusing a selected gas into a selected volume of water, it is understood that any appropriate fluid, such as a liquid, may be infused with the gas with infusion system 20. Therefore, water is merely exemplary.

In various embodiments, water being infused with the gas may include a selected or first volume of water to allow for treatment of a second volume of water. The final treated volume may include a wastewater treatment tank/pond, an aquaculture system, an irrigation volume of water, a natural body of water such as a lake, river, or stream, or the like. Thus, the volume of water that is treated with the infusion system 20 may be used for any appropriate purposes such as cleaning or sterilization of a surface, cleaning or sterilization of a large volume of water, or assisting in other processes, such as irrigation and aquaculture.

Further, the treatment provided by the infused water, such as the initial or auxiliary treated volume may be used for destruction and/or neutralization of selected species. Species may include the chemical species such as selected one or more Per- and Polyfluorinated Substances (PFAS) including those referred to as perfluorooctane sulfonate (PFOS) and or perfluorooctanoic acid (PFOA). Various other chemical species may also be degraded, in addition to PFAS including short-chain PFAS. Also, various biological organisms may be destroyed or inactivated, such as various bacteria, molds, fungi, or other species including blue green algae (cyanobacteria) and Red Tide (Karenia). Thus, the treated water may be used for various purposes such as cleaning and/or treating of various water sources or volumes to assist in cleaning and making them safer for human or other animal consumption and/or contact and to assist in various activities such as disease, virus, and bacteria control and/or growth augmentation agriculture and/or aquaculture.

The infusion system 20 may include various components to allow for the inflow and outflow of a fluid including a liquid. In various embodiments, the liquid may be water. The mixing system 20 further includes components that allow and/or control inflow of a gas, such as a plasma-activated gas. The plasma-activated gas may be generated by any appropriate system, including those discussed further herein. Additional exemplary plasma-activated gas generation system may include a PAG generator 28, as illustrated in FIG. 5. The PAG generator 28 may include a generator portion 32 housed within a housing 34. The PAG system 28 may include that described in U.S. Pat. Nos. 10,797,472 and/or 10,032,593 both to In Ho Lee et al., all of the above incorporated herein by reference. As noted above, however, additional and/or alternative PAG generation systems may also be included such as those disclosed in U.S. Pat. No. 9,352,984 and U.S. Patent Application Publication 2016/0102025, all of the above incorporated herein by reference. Nevertheless, the PAG may also be generated with the system as discussed further herein.

The PAG, however, may be infused into a selected volume of a liquid, such as water, as noted above, with the infusion system 20, as illustrated in FIGS. 1, 2, 3, and 4. The infusion system 20 may be powered by a pump, such as a submersible pump 40 that is positioned within the container 24 and/or other appropriate volume. According to various embodiments, the pump 40 may be positioned within an internal container 41 within the container 24. The liquid may overflow or fill into the container 41 and is then pumped with the pump 40 to the inlet 44.

The target constituent may be more or less dense than water. The liquid to be treated may be collected from the area expected to have the highest concentration. Similarly, the target constituent may be concentrated at the surface because of dissolved air floatation and/or foam fractionation. The inlet can be modified (e.g., moved or positioned) to capture either the bottom liquid or the surface liquid to provide preferential treatment through multiple infusions of PAG to the most concentrated contaminants. It is understood that the pump 40 need not be a submersible pump but may also be a dry pump that is positioned external to the volume, such as the container 24, and powers a flow of fluid, such as liquid including water, through the infusion system 20 while drawing water from the container 24 and through the infusion system 20. However, the submersible pump allows for a compact system, such as the self-contained PAG infusion system illustrated in FIG. 1. As noted above, a self-contained infusion system 25 is not required, however, the self-contained infusion system 25 may allow for portability and production of a plurality of systems for various applications that may be efficiently moved from location to location and/or manufactured for purchase at selected locations.

The self-contained system 25 may allow for the submersible pump to pump water within the container 24 to an infusion inlet 44. The infusion inlet 44 may be connected to the submersible pump 40 through a connection, such as any appropriate fluid connection 48. The submersible pump 40 may be powered through any appropriate power mechanism such as a power cord, an internal power system, or other appropriate power system. The submersible pump 40 may pump water through the connection 48 to the infusion inlet 44. The infusion system may then include an outlet 52 to allow the water that has been infused with a plasma-activated gas to reenter the container 24. The outlet can include a device to minimize the discharge of excess (non-dissolved) PAG as bubbles to increase the amount of gas delivered and improve the treatment process.

The self-contained infusion system 25 may allow for a recirculation of liquid, such as water, from the container 24. The average number of passes (through recirculation) is controlled by the rate at which untreated water is introduced into container 24 and can be varied to account for the treatability of the species of interested in the targeted water. Various operation parameters may be augmented or changed based upon a selected application for the plasma-activated infused water in the container 24. Various parameters that may be adjusted include a flow rate of gas to the infusion system 20, flow rate and pressure of water through the infusion system 20, a concentration of selected species in the gas to the infusion system 20, and other appropriate parameters.

Varying the influent rate into container 24 varies the number of times the water volume is re-infused with PAG allowing the PAG and its byproducts, including ozone, to become supersaturated in containers 24 even as the treated water consumes the radicals generated by the PAG. The number of recirculations, which can increase the PAG concentration in the liquid, is increased for highly concentrated influent (i.e., concentrated with the species of interest) and/or difficult to destroy chemicals. Also, as noted above, the system may include modifications to capture and recirculate surface liquid (e.g., water) take advantage of dissolved air flotation and/or foam fractionation.

With continuing reference to FIG. 1 and additional reference to FIGS. 2-4, the infusion system 20 will be described in further detail. In various embodiments, the infusion system 20 need not be connected directly to the container 24 for the self-contained infusion system 25. Accordingly, the infusion system 20 as discussed further herein, will be understood to be operable with an appropriate volume of liquid, such as water, which may include the container 24 or other appropriate volumes, or other appropriate volumes. For example, the infusion system 20 may be hydraulically connected to a pond, such as a wastewater treatment tank, for treatment of the water therein.

The infusion system 20 includes the inlet 44 and the outlet 52. The infusion system 20 further includes an inlet manifold 54 and an outlet manifold 58. The manifolds 54, 58 allow for equally distributing pressure and flow and positioning of one or more infusion portions 62 between the two manifolds 54, 58. Any appropriate number of infusion portions 62 may be provided based upon selected parameters, such as a desired volume of gas to be infused, the concentration of the infused gas, a volume and rate of water to be treated, the concentration of the species of interest, the difficulty of treatment of the species of interest, a flow rate through the infusion system 20, or other selected parameters including the quality of the influent and the required effluent quality. For each of the infusion portions may be an inlet valve 59 and an outlet valve 61. Thus, each infusion portion 62 may be individually controlled. Also, the valves 59, 61 may include pressure and/or flow meters. Also, they may be automatically controlled. The infusion portions 62 may be one or more of a venturi injector, an aeration device, and/or a gas dissolution pressure tank.

Exemplary operation conditions may include a continuous waste stream of highly PFAS contaminated landfill leachate Reverse Osmosis reject water. This leachate water may be treated at a rate of 1,500 gallon per day, utilizing 16 infusers portions, each delivering between two to three liters per minute of PAG, using air as a carrier gas, delivering PAG with an Ozone content exceeding 5 parts per million (ppm). The treated effluent met federal guidance (PFOA+PFAS<70 part per trillion (ppt)), Michigan groundwater standards (PFOS<16 ppt and PFOA<8 ppt), and all but one of the Michigan Drinking Water Standards. Of fifteen detectable PFAS constituents, nine were destroyed (below the detection limit), and six were reduced. Similar results were demonstrated on identical wastewater operating at a treatment rate of 3,000 gallons per day. Thirteen of the PFAS constituents were detectable in the influent. Eight of the detectable constituents were destroyed (below detection limits), and five were reduced. Without being bound by the theory, and only as an example, when this same waste stream is partially treated PFAS constituents can be disassociated and recombine as a different PFAS constituent. For example, when the same waste stream was treated at a rate of 7,600 gallons per day with three infusers injecting PAG using air a as carrier gas and another three infusers injecting PAG using argon as a carrier gas, results did not achieve the same rates of reduction. Of the twelve detectable constituents, one constituent was destroyed, five were reduced.

As one skilled in the art will understand, therefore, the infusion portion 62 may include a plurality of individual infusion portions 62a having substantially similar components, such as those discussed further herein. Accordingly, discussion of the single one infusion portion 62a will be understood to be replicated by the other infusion portion and the discussion of a single one of the infusion portion 62a is merely exemplary.

Each infusion portion 62a, therefore, may include a water inflow conduit 64 that allows flow of water from the inlet manifold 54 into the infusion portion 62a. The infusion portion 62a further includes an outflow portion or conduit portion 68 that allows flow of water from the infusion portion 62a to the outlet manifold 58. In this way, water may flow into the infusion portion 62a and through an infusion member 72.

The infusion member 72 may be any appropriate infusion member, such as a Mazzei® injector venturi port sold by Mazzei Injector Company, LLC having a place of business in Bakersfield, California. Various exemplary Mazzei® injector ports include the model number 584 that includes an inlet side 74 and an outlet side 76. Between the inlet and outlet sides 74, 76 is a barb 80 that may be a gas connection, as discussed further herein.

Downstream of the infusing member 72, such as downstream of the outlet 76, may be a viewing or inspection port or portion 84 of the infuser portion 62*a*. The inspection portion 84 may allow for visual inspection of a flow of material past the infusion member 72. The inspection port 84 may allow for inspection of the passage of debris, the presence of bubbles, the presence of turbulence, or other visual features in the flow. It is understood that the visual inspection may be automatic and/or manual, such as with a user. An automatic inspection may include a camera system, a bubble monitor (such as a Siansonic Air Bubble Detector), or a solids monitor (such as a Pyxis RT-100 PRISM inline Refractometer) and various appropriate associated processor systems to visually inspect the flow in the inspection portion 84.

Accordingly, the infusion portions 62 may include one or more of the infusion portion 62*a*. The infusion portion 62 allow for a passage of the liquid, such as water, from the inlet manifold 54 to the outlet manifold 58. The infusion portion further includes a flow path of the fluid, such as water, to and/or through the infusion member 72.

The infusion system 20 may further include various controls such as an inlet or influent control valve 90 that may be used to control or stop flow into the infusion system 20. In various embodiments, various valves and couplings can be included to allow for isolation, removal, and repair of individual infusers without eliminating flow to the other infusers. The infusion system 20 may include an effluent or outflow valve 94 such as to control outflow from the infusion system 20. The infusion system 20 may include a bypass valve 98 that allows for a passage of fluid between the inlet 44 and the outlet 52 to control the flow rate and pressure drop of the fluid flowing through the infusion portions 62.

The infusion system 20 may further include a gas valve 102 that controls a flow of gas into the infusion members 72 such as via the gas inlet 80, as discussed further herein. Accordingly, various valves or controls may be used to control a flow of liquid to the infusion portion 62 from the inlet 44 to the outlet 52. Also, a gas control 102 may control the flowrate of gas to the individual infusion member 72. Again, as discussed above, any appropriate fluid may be used to be infused in the infusion system 20. In various embodiments, the fluid that flows through the inlet and outlet 44, 52 may be a liquid and a gas through the gas inlet 102. In various embodiments, including those discussed further herein, the fluid flowing through the inlet and outlet 44, 52 may be water and the gas may be PAG. The rate of flow and/or the on and off of the flow of the PAG may be controlled with the valve 102.

The infusion system 20 may further include various meters or sensors, such as a flow meter 106 to sense or detect flow volume and rate of the water through the infusion system 20. Additionally, one or more pressure gauges, such as a first pressure gauge 108 upstream of the bypass valve 98 and a second pressure meter 110 downstream of the bypass valve 98 may be provided to, select, including optimize gas delivery. The flow meter 106 may be used to determine a flowrate and volume through the infusion system 20 of the water (Micronics U1000 Clamp on Flow Meter). The pressure sensors 108, 110 may be used to optimize gas delivery by controlling the pressure within various portions of the system, such as on an inlet or outlet side.

Figure 3:
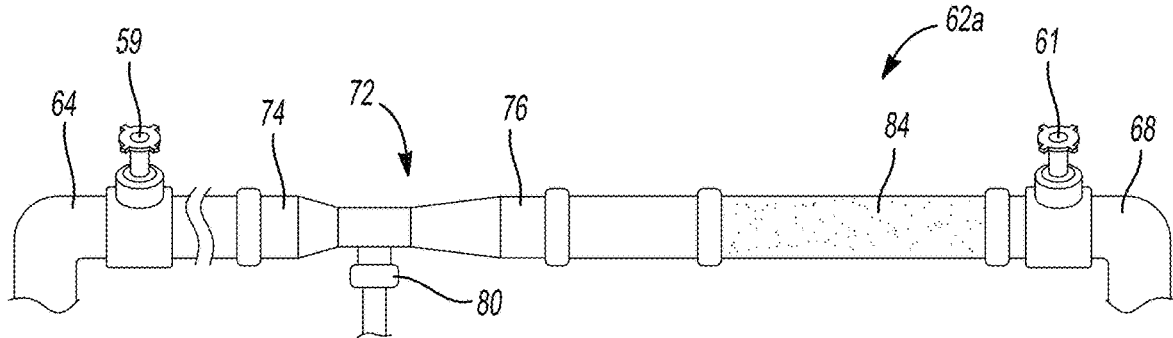
FIG. 3 is a detail schematic view of a portion of the gas infusion system of FIG. 1, according to various embodiments.
Figure 4:
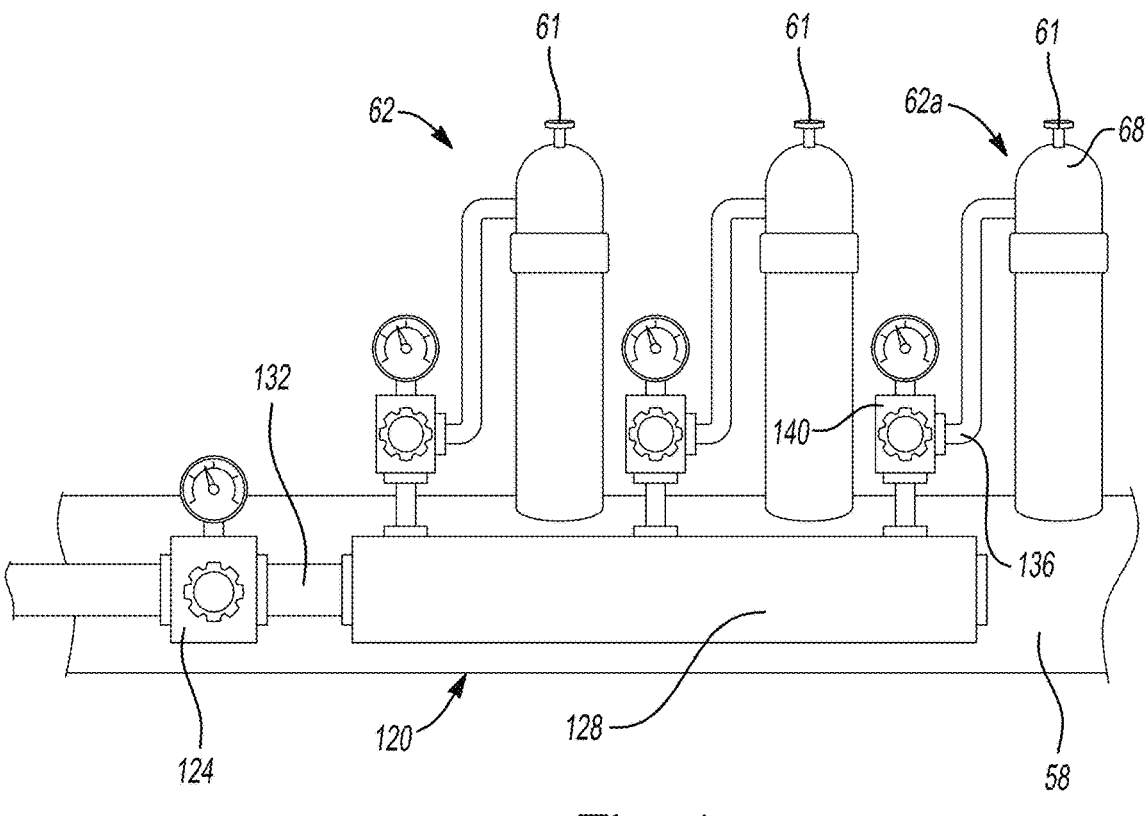
FIG. 4 is a detail schematic view of a portion of the gas infusion system of FIG. 1, according to various embodiments.

With continuing reference to FIGS. 1-3 and additional reference to FIG. 4, the infusion system 20, including the infusion portion 62, may include a gas supply system 120 having an inlet 156 from a gas source, such as Plasma Activated Gas (PAG) as discussed herein. The gas supply system may initially receive gas through the gas shutoff valve 102 into an initial or main flow control regulator and/or meter 124. The main regulator 124 may allow for regulation of a flow to a gas distribution manifold 128 for the gas. The gas manifold 128 allows for distribution of a supply of gas to all of the infusion portions 62 including each of the individual infusion members 72. The gas may flow from the main regulator 124 through a first conduit 132 to the manifold 128. From the manifold 128, gas may flow to each of the individual infusion members 72 via an outflow conduit 136.

The outflow conduit 136 may initially be connected to an individual regulator and/or flow meter 140. The individual regulator flow meter 140 allows for a regulation and flow determination to each individual infusion member 72 and to distribute the gas, such as equally, between multiple infusion members 72. Therefore, an inflow to the manifold 128 may be regulated by the main regulator 124 and a flow to each of the individual infusion member 72 may be regulated by the individual regulators 140. Thus, a gas flow to each of the individual infusion portion 62 may be separately measured and/or regulated.

According to various embodiments, the gas, including the PAG, may be provided to the infusion portions at a selected pressure. The pressure may be appropriate for the selected system, including the infusion members 72. In various embodiments, however, the pressure may be about 50 psi to about 500 psi, including about 100 psi to about 300 psi.

The gas flow rates that are measured with the flow meters 124, 140 may be automatic and/or manual. In various embodiments, for example, a digital flow meter may be used to measure a flow and data may be collected with a processor module. Further, the flow meters and regulators 124, 140 may also be manually adjusted and/or automatically adjusted. For example, a selected flow rate may be determined for operation of the infusion system 20. Therefore, the flow meters and regulators 124, 140 may be monitored and/or adjusted to achieve a selected flow rate to each of the individual infusion member 72 of the infusion portion 62. Flow monitors and/or controllers may be automated and control the processor modules. Exemplary automated liquid flow systems include Micronics U1000 Clamp on Flow Meter and gas flow rate systems include Bronkhorst Flexi-Flow meter. These monitors allow automated matching of water flows with gas delivery as well as remote monitoring of operation and further allows fouled infusers to alarm and allow the individual infuser to be taken offline and the gas delivery to be redistributed to the functioning infusers until maintenance can be performed.

Each of the infusion members 72 may be or include a venturi style valve. Accordingly, the flow of the water through the infusion system 20 may provide a selected force to draw the PAG into the water as it passes each of the individual infusers 72. This design, according to various embodiments, also allows the PAG to be delivered under pressure for increased gas concentration (including super saturation) and increase dissolved PAG delivery at point of delivery. Therefore, a flow rate of water may change or adjust a flow of the gas into the infusion member 72. In turn, control of the inlet and outlet valves 90, 94 and/or the submersible pump 40 may be selected and controlled to control a flow of the gas into the individual infuser 72. Again, each of these controls may be controlled with a processor module to assist in maintaining or achieving a selected flow rate of the water through the infusion system 20 and/or gas into the infusion system 20.

Returning reference briefly to FIG. 1, the infusion system 25 may further include a separate and/or complementary gas infusion system. The secondary or complementary gas infusion system may receive water via a conduit 52' including some or all of the outlet liquid from outlet 52 of the gas infusion system or act independently and withdraw water from the tank 24. The complementary gas infusion system may include an inlet 156' that may also receive the PAG from the generator, similar to the inlet 156. The PAG may flow to a containment system or area 159 that may include one or more nozzles or outlets 161. The outlets 161 discharge a selected volume of supersaturated water with a selected size of bubbles. The bubbles may include a selected size, such as at nanometer diameter sizes, as discussed herein. The bubbles generally flow in the direction of arrow 167. The gas bubbles that include PAG from the inlet 156' further incorporate gas into the volume of liquid within the container 24. Therefore, the infusion system 25, including the infusion portions 62 may be enhanced and/or augmented by the further infusion by the gas from the nanometers bubbles from the inlets, which may be tubes, 161.

The process described herein may improve, according to various embodiments, the gas delivery by infusing PAG and delivering that gas as a micro- or nano-bubble. The amount of PAG delivered can be increased using micro- or nano-bubble, without being bound by the theory, because the surface area of the gas/liquid interface is increased several orders of magnitude and micro- or nano-bubbles will have much longer contact time with the liquid. For example, because buoyancy is small, nanobubbles, in particular, are sufficiently small that bubbles do not rise but rather behave in a manner similar to Brownian motion. An additional benefit is the increase in the generation of hydroxyl radicals (OH⁻) caused by bubble collapse. As gas leaves the bubble to dissolve in the liquid (and become available for treatment or acting on the selected species), the bubbles shrink and eventually collapse causing an energy discharge leading to additional radicals for treatment of the selected species. Because one microbubble delivers the same volume of gas as 1 million nanobubbles, nanobubbles are expected to generate a million more collapses and a corresponding number of additional radicals.

The efficiency of gas-liquid transfer can be improved using nanobubbles because the mass transfer rate of a gas depends on the mass transfer area of the gas-liquid phases which are much higher for nanobubbles and accordingly can cause the gas dissolution rate in water to reach supersaturation state. Additionally, the number of bubbles available for collapse is several orders of magnitude higher for the same volume of gas delivered. Bubble collapse causes the disappearance of the gas-liquid interface, and during the process of nanobubble self-pressurizing, an extremely high concentration of charged ions is accumulated at the interface to that will instantly release chemical energy that generates hydroxyl radicals (OH⁻). This further contributes to the chemical oxidation of the PAG infused wastewater.

Micro/nanobubbles can be generated in a number of ways such as disclosed in "A critical review of the recent developments in micro-nano bubbles applications for domestic and industrial wastewater treatment", Sakr, Mohamed, Maraqa, Hamouda, Hassan, Ali, Jung, Alexandrria Engineering Journal, 61:8, pp 6591-6612 (Feb. 2, 2022) at www.sciencedirect.com/science/article/pii/ S1110016821007742?via %3Di hub. Additional and/or alternative methods include venturi infusion, water vortex microbubble generation, and pressurization followed by depressurization such as that described in U.S. Pat. No. 9,308,505, incorporated herein by reference.

The PAG generator 28 can include various systems, such as those discussed above. For example, the PAG generator 28, as illustrated in FIG. 5, may include the PAG generation portion 32. The PAG may be collected or originally generated in a PAG volume 150. The PAG volume 150 may include an initial volume of the PAG generated by the PAG generator 28. The PAG from the PAG volume may be transported from the PAG volume 150 to the infuser system 20. In various embodiments, an outlet conduit 154 may connect to the PAG volume 150 and the infuser 20, such as at an inlet 156 wherein the control valve 102 may control flow of the PAG to the infuser system 20. As discussed above, the individual infuser member 72 may operate on a venturi valve system such that flow of the water through the infuser system 20 causes flow of the PAG through the conduit 154 from the PAG volume 150.

The PAG may be generated, as discussed above, and may require a fresh supply of gas, such as atmospheric air. Accordingly, an air conduit 160 may allow inlet or inflow of air into the PAG volume 150. The air may be atmospheric air and, therefore, may be filtered through a filter 164 before entering the conduit 160 to enter the PAG volume 150. Thus, the PAG generator 28 may generate the PAG for being transferred to the infuser system 20.

The infuser system 20 may operate with the venturi valve system, such that the flow of the water may cause or provide a force to cause the PAG to be drawn into the infuser member 72. In addition, and/or alternatively thereto, it is understood that the flow of the PAG from the PAG generator 28, including the PAG volume 150, may be active due to a pump, fan 168, compressor, or the like to provide a selected flow through the outlet conduit 154 to the infuser 20. Thus, the PAG may flow from the PAG volume 150 generally in the direction of arrow 172 from the PAG volume 150 to the infuser 20.

Turning reference to FIG. 6A, according to various embodiments, a PAG generator 200 is illustrated. The PAG generator 200 may include various portions similar to the PAG generator 28, discussed above. The PAG generator 200, however, may include an operation that differs from the PAG generator 28 and allows for a continuous flow of gas through the PAG generator 200 without requiring a PAG volume 150, as discussed above.

According to various embodiments, the PAG generator 200 is designed to operate under pressure, closer to a gas mixing (e.g., infusion) location in a larger treatment operation. The PAG generator 200 may include any appropriate length and PAG generation portions, as discussed herein, for placement in a PAG system. The PAG generator 200, however, may provide a streamlined and in situ configuration compared to the PAG generator 28.

The PAG generator 200 may include a housing or channel wall 204. The channel 204 may include one or more portions that are separated, as discussed herein. For example, the channel 204 may include a first or corona portion 204a that allows for a flow of gas generally in the direction of arrow 208. The channel 204 may further include a secondary flow portion 204b for generated PAG. The flow of gas may enter at an inlet end 212 of the channel 204 in the corona portion 204a and exit at an exit end 218 of the channel 204 in the secondary flow portion. To achieve this, the gas must pass through the plate 228. It is understood that the PAG generator 200 may include any appropriate length and/or that a PAG generator includes a plurality of the channels 204.

Nevertheless, the single example will be discussed here. The channel 204 may also be positioned within a housing or cabinet, 219, if selected.

The channel 204 has a substantially unobstructed flow path 220 from a PAG generation volume or area 224 in the channel portion 204a to the outlet portion 204b. The flow path 220 of the channel 204 may be separated such that the inlet portion 204a near the PAG generation volume 224 is separated from the outlet portion 204b by a plate 228. The plate 228 may be grounded, as discussed further herein, and/or electrically isolated from a voltage source 229. The plate 228 may include one or more passages 232 to allow charged particles, such as electrons and/or other species including PAG, to pass from the generation area 224 to the outlet portion 204b, such as generally the direction of arrow 236. The passages may be sized for selected purposes, such as the specific voltage applied and/or the volume of gas flow, etc. The size of the passage may include a cross-section area of about 0.1 millimeters squared ($mm^2$) to about 100 $mm^2$, including about 0.1 $mm^2$ to about 10 $mm^2$, and further including about 10 $mm^2$.

Spaced away from the plate 228 may be one or more generation points 240 of generation members (also referred to as pins) 242 that extend from a support 244 a selected distance 248 from the plate 228. The distance 248 may be selected for various purposes, as discussed further herein. For example, the distance 248 may be about 0.1 mm to about 20 mm, including about 3 mm to about 10 mm, and further including about 8 mm. The generation members 242 may also include a selected cross-sectional dimension such as about 1 mm to about 20 mm in diameter.

The generation point 240 is electrically connected to a power source or power transmission source 252 through an electrical connection 256. The power source 252 may provide a selected or cause a selected voltage at the generation point 240. The voltage causes a generation of corona around the point or relative to the point 240. The voltage can be generated by taking low voltage, low power, such as from a 12 volt, 26.7 amp universal DC power supply (XP Power LCW320PS12) and multiplying the voltage using an astable multivibrator to generate an appropriate voltage such as about 9,000 volts, including about 5,000 volts to about 15,000 volts. In various embodiments, a selected voltage is delivered to the point 240, using an astable multivibrator or equivalent. The placement and distances of the pins and plate can be varied but, in various embodiments, the voltage is elevated to 9,000 volts and is directed to a pin centered above a 10 millimeter hole on the plate 228. The corona caused at the point 240 may generate electrons that are accelerated toward the plate 228 as the plate 228 may be charged positively, such as by connection to the power source 252 as schematically illustrated in FIG. 6.

As the electrons are accelerated to the plate 228 at least a portion may pass through the bores or holes 232 to enter the channel 220. As air passes through the channel 220, the electrons may cause the formation of selected ions or other appropriate species in the gas as it flows through the channel 220. The gas flowing through the channel 220 may therefore become the plasma-activated gas (PAG) that exits the exit end 218 for a selected purpose. As discussed above, the exit 218 may be connected to the infuser 20 for infusion of the PAG into water, as discussed above.

The generation of the PAG in the PAG generator 200 may be altered according to various parameters. For example, the voltage applied with the power source 252 may be varied. The distance 248 of the point 240 from the plate 228 may be altered or adjusted to assist in causing a higher number or concentration of electrons accelerating through the passages 232. The size of the passage 232 may also be altered or adjusted. The passage 232 and/or other portions, such as the plate 228, may be insulated to minimize electron loss after passing through the corona. The pressure under which it is operated may increase as a method of increasing the saturation concentration of the generated gases—notably ozone. Other parameters may include a flow rate of the gas through the tube 204 to either increase a flow and movement of electrons through the PAG generator 200 and/or allow a greater dwell time of a selected volume of a gas to allow for a greater number of electrons to disrupt the oxygen and/or nitrogen in the carrier gas thereby making the resulting PAG more aggressive in attaching the target pollutant.

According to various embodiments, PFAS can be destroyed (below detection) when treated with GAL. However, if PAG and/or GAL concentration is insufficient and/or the residence time is insufficient, PFAS can be disrupted but then recombined to form other, shorter-chain PFAS. For example, when a continuous waste stream of highly PFAS contaminated landfill leachate Reverse Osmosis reject water was treated at a rate of 1,500 gallon per day, utilizing 16 venturi infusers, each delivering between two to three liters per minute of PAG, using air as a carrier gas, delivering PAG with an Ozone content exceeding 5 ppm. The treated effluent met federal guidance (PFOA+PFAS<70 ppt), Michigan groundwater standards (PFOS<16 ppt and PFOA<8 ppt), and all but one of the Michigan Drinking Water Standards. Of fifteen detectable PFAS constituents, nine were destroyed (below the detection limit), and six were reduced. Similar results were demonstrated on identical wastewater operating at a treatment rate of 3,000 gallons per day. Thirteen of the PFAS constituents were detectable in the influent. Eight of the detectable constituents were destroyed (below detection limits), and five were reduced.

In various embodiments, without being bound by the theory, the corona at the points 240 cause electrons to be freed and/or generates free electrons that may accelerate through the bore 232 in the plate 228. Generally, the material of the plate 228 and the pins 242 is conductive, but once the PAG is generated and passes through the holes 232, the tubing and the underside of the plate 228 can be insulated to minimize the loss of charged radicals. These electrons may interact with various chemical species in the air to change those species. For example, oxygen or nitrogen radicals may be formed, hydroxyls may be formed, and/or other appropriate or selected chemical species may be formed due to the presence of the energized electrons. The gas passing through the PAG generator 200 therefore becomes plasma-activated gas with the selected chemical species, including radicals therein. Again, without being bound by the theory, a higher flow rate may dilute the radicals generated in the PAG due to the speed and minimal dwell time of species that might be affected by the electrons within the PAG 200. A low flow rate, however, may also not allow a large enough number of particles for exposure to the electrons before the electrons are either absorbed into the casing 204, the plate 228, or may deliver a larger portion of non-activated species.

Turning reference to FIG. 6B, a generator 200' is illustrated. The generator 200' may be substantially identical to the generator 200, discussed above. The generator 200', however, includes the channel 204 that is unobstructed and allows a flow of gas through portions near the members 242 and opposite the members 242 relative to the plate to 228. Thus, a flow through the chamber 218 of the generator 200' may be unobstructed relative to the channel 204. It is understood, therefore, in the housing 218 a flow on either side of the plate 228 may be restricted such as to first flow near the pins 240 and then through the plate 228 to the opposite side of the plate 228 from the 240 pins, as illustrated in FIG. 6A, or have an unobstructed path as illustrated in FIG. 6B. The generator 200', however, may be operated substantially identically to the generated 200 as discussed above.

The PAG may be used for various purposes, such as generating oxygen and nitrogen radical gas—including ozone—for use as a gas or to be infused into a liquid, such as water, as discussed above, to generate the GAL. The water may be used for various purposes such as for cleaning the water by direct application of the PAG to the water such as through the infusion process discussed above and/or mixing of the infused water with other water sources. This may be used to destroy or neutralize various chemical species, such as PFAS. The activated gas and/or infused water (GAL) may also be used for killing or inactivating various biological species such as bacteria, fungus, and/or viruses as well as destruction and/or control of blue green algae (cyanobacteria) and/or red tide (Karenia). This may assist in decreasing pathogen growth, controlling odors, and other purposes. The destruction of selected chemical species and/or for killing or neutralizing various organisms may assist in enhancing desired growth (e.g., agriculture) and reducing undesirable growth such as in the food packaging, food processing facilities, and the like.

The PAG may also be applied directly onto various surfaces. For example, the PAG may apply directly to an air transport system to assist in neutralizing and/or destroying chemical species and/or organisms on plant surfaces, such as leaves. This may assist in *cannabis* growth operations, aquaculture, and other purposes. Further the PAG may be applied to surfaces to assist in disinfecting the same.

The system, according to various embodiments as discussed herein, may be used to generate PAG and/or PAL. The PAL and/or PAG may be an effective treatment for destruction of VOCs, removal of metals, total suspended solids, organic carbon and many, many more as well as significant reductions to chemical oxidation demand (COD). Additionally, PAG is used for disinfection in food processing operations, disinfection, odor control, plant growth stimulation, virus, fungus, and bacteria control in hydroponics operations.

In addition to the PAG generator 28, 200, as discussed above, various other systems may also be added to assist in various cleaning and/or sterilization applications. For example, an ultraviolet generator, such as an ultraviolet light 300, may be added within the casing 204 to further assist in sterilizing or cleaning the flow through the PAG generator 200.

The systems according to various embodiments may be operated to achieve selected results. For example, for difficult to destroy, complex organic chemicals, such as PFAS, repeated infusion of high concentration PAG may be used to fully destroy the target chemical or target species. In the case of PFAS, the chemical may disassociate with the introduction of PAG, but the fragments of chemical will recombine to form other smaller chain PFAS. Repeated infusion of PAG destroys the molecules and the concentration of the entire family of PFAS becomes below detection limits. The repeated treatment with PAG may be by provided a plurality of infusers in series and/or several as ones as illustrated above. In various embodiments, a bulk volume of contaminated liquid may be treated and bulk treated serially to achieve selected results.

For less complex treatment, like destruction of Blue Green Algae (Cyanobacteria) or Red Tide (Karenia), the number of treatment steps may be reduced to as low as one. The introduction of PAG will destroy the live biological species of concern and once destroyed, it will not regenerate. Thus, if the amount and concentration of PAG is sufficient to inactivate all of the biological species, a single pass may suffice.

Moreover, the PAG alone may be introduced into an environment. For example, in a packaging center, PAG may be introduced into the environment, such as with a HVAC system, to assist in cleaning and/or sterilizing items to be packaged. This process may also control and/or eliminate air borne diseases including bacteria such as *legionella* (causing a type of pneumonia known as Legionnaires' disease). This may enhance and/or increase longevity, cleanliness, etc. of packaged items such as food. Similarly, PAG may be introduced onto plants or other surfaces to decrease and/or eliminated selected species.

Example embodiments are provided so that this disclosure will be thorough and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail. It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors or processor modules, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed:

1. A gas and fluid mixing system comprising:
a fluid inlet;
an inlet fluid manifold coupled to the fluid inlet;
a fluid outlet;
an outlet fluid manifold coupled to the fluid outlet;
a gas distribution manifold having a gas inlet;
a plurality of fluid conduits between the inlet fluid manifold and the outlet fluid manifold;
an infusing member in each fluid conduit; and
a gas conduit coupled to each infusing member from the gas distribution manifold;
wherein a fluid is operable to enter the fluid inlet and flow to the fluid outlet through the inlet fluid manifold, the plurality of fluid conduits, and the outlet fluid manifold while being infused with a gas at each infusing member from the gas inlet through the gas distribution manifold to each gas conduit;
wherein each of the fluid conduits extend and allow for fluid flow between the inlet fluid manifold and the outlet fluid manifold.

2. The mixing system of claim 1, further comprising:
a gas generator system configured to generate a selected gas, wherein the concentration of the generated gas may be varied by varying a voltage, a pin to plate distance, and a bore hole in a plate, a number of corona generating points, and the amount and rate of carrier gas drawn through the gas generator system.

3. The mixing system of claim 2, wherein the gas generator system is configured to generate a plasma activated gas by forming a plasma within a flow of a gas.

4. The mixing system of claim 2, wherein the gas generator system comprises:
a channel extending from a first end to a second end;
a plate separating a first portion from a second portion between the first end and the second end;
at least one corona generating member positioned a distance from the plate; and
a generator configured to generate a voltage at the corona generating member relative to the plate;
wherein a gas is operable to flow from the first end to the second end.

5. The mixing system of claim 4, wherein the plate includes at least one hole through which an electron is operable to travel to affect the gas.

6. The mixing system of claim 1, wherein the each infusing member includes at least one of an infuser, a pressurized vessel, or a venturi injector.

7. The mixing system of claim 6, wherein gas is drawn into the flow of the fluid by the venturi effect.

8. The mixing system of claim 1, further comprising:
a gas flow regulator;
wherein the gas flow regulator regulates a flow of the gas from the gas inlet to the gas distribution manifold.

9. A plasma activated gas (PAG) generating system operable to generate PAG, comprising:

a casing extending from a first end to a second end;
a plate separating a first portion of the casing from a second portion of the casing between the first end and the second end of the casing;
at least one corona generating member positioned a distance from the plate; and
a generator configured to generate a voltage at the generating member relative to the plate;
wherein the plate includes at least one hole through which an electron is operable to travel to affect a gas;
wherein gas is operable to flow from the first end of the casing in the first portion of the casing to the second end of the casing in the second portion of the casing.

10. The system of claim 9, further comprising:
a mixing system comprising:
a fluid inlet;
a fluid outlet;
a gas inlet;
a fluid conduit between the fluid inlet and the fluid outlet;
an infusing member in the fluid conduit; and
a gas conduit to the infusing member from the gas inlet;
wherein a fluid is operable to enter the fluid inlet and flow to the fluid outlet through the fluid conduit while being infused with a gas at the infusing member from the gas inlet.

11. The system of claim 10, wherein the infusing member includes at least one of a venturi injector, an aeration device, or a gas dissolution pressure tank.

12. The system of claim 11, wherein gas is drawn into the flow of the fluid by the venturi effect.

13. The system of claim 10, further comprising:
an inlet fluid manifold coupled to the fluid inlet; and
an outlet fluid manifold coupled to the fluid outlet;
wherein the fluid conduit includes a plurality of fluid conduits;
wherein each of the fluid conduits extend and allow for fluid flow between the inlet fluid manifold and the outlet fluid manifold.

14. The system of claim 13, wherein the infusing member includes a plurality of the infusing members;
wherein each fluid conduit of the plurality of fluid conduits includes at least one of the infusing members.

15. The system of claim 10, further comprising:
a gas flow regulator;
wherein the gas flow regulator regulates a flow of the gas from the gas inlet to the infusing member.

16. A gas and fluid mixing system comprising:
a fluid inlet;
a fluid outlet;
a gas inlet;
an infusing means of introducing the gas into a fluid including;
(i) an infusion system including a means of infusing gas into a liquid including a venturi valve; and
(ii) a complementary saturation and/or supersaturation system including a means to spray a fluid, under pressure, through plasma activated gas under pressure;
a fluid conduit between the fluid inlet and the fluid outlet; and
a gas conduit to the infusing means from the gas inlet;
wherein a fluid is operable to enter the fluid inlet and flow to the fluid outlet through the fluid conduit while being infused with a gas at the infusing means from the gas inlet.

17. The system of claim 9, wherein the first portion of the casing is open on the first end and closed on the second end and the second portion of the casing is closed on the first end and open on the second end, wherein the gas is capable to flow into the first end at the first portion, through the at least one hole in the plate, and exit from the second portion of the casing at the second end.

18. The mixing system of claim 1, wherein each fluid conduit includes an inspection portion to allow for visual inspection of a flow of fluid through each fluid conduit.

19. The mixing system of claim 1, further comprising a bypass conduit between the intake fluid manual manifold and the outlet fluid manifold operable to bypass the fluid past each infusing member.

\* \* \* \* \*